United States Patent
Boccellato

(10) Patent No.: US 10,317,304 B2
(45) Date of Patent: Jun. 11, 2019

(54) SCREWDRIVER TEST BENCH

(71) Applicant: SCS CONCEPT ITALIA SRL, Cusano Milanino (IT)

(72) Inventor: Roberto Boccellato, Seriate (IT)

(73) Assignee: SCS CONCEPT S.R.L., Cusano Milanino (IT)

( * ) Notice: Subject to any disclaimer, the term of this patent is extended or adjusted under 35 U.S.C. 154(b) by 32 days.

(21) Appl. No.: 15/539,319

(22) PCT Filed: Dec. 21, 2015

(86) PCT No.: PCT/IB2015/059828
§ 371 (c)(1),
(2) Date: Jun. 23, 2017

(87) PCT Pub. No.: WO2016/103150
PCT Pub. Date: Jun. 30, 2016

(65) Prior Publication Data
US 2017/0363500 A1    Dec. 21, 2017

(30) Foreign Application Priority Data

Dec. 23, 2014 (IT) .............................. MI2014A2239

(51) Int. Cl.
*G01N 3/22* (2006.01)
*G01L 25/00* (2006.01)
(Continued)

(52) U.S. Cl.
CPC ............ *G01L 25/003* (2013.01); *B25H 1/005* (2013.01); *G01L 3/20* (2013.01); *G01N 3/22* (2013.01); *B25B 21/00* (2013.01)

(58) Field of Classification Search
CPC ........ G01L 25/003; G01N 3/22; B25H 1/005; B25H 21/00
See application file for complete search history.

(56) References Cited

U.S. PATENT DOCUMENTS 3,314,458 A * 4/1967 Weber ..................... B25B 21/00
81/430
3,321,962 A * 5/1967 Grady .................. G01L 25/003
73/1.09
(Continued)

FOREIGN PATENT DOCUMENTS

CN    101634862 A    1/2010
CN    103713519 A    4/2014

OTHER PUBLICATIONS

Machine translation of CN 101634862 A.*
(Continued)

*Primary Examiner* — David J Bolduc
(74) *Attorney, Agent, or Firm* — Perkins Coie LLP; Viola T. Kung; Andrew T. Pettit

(57) ABSTRACT

A test bench for screwdrivers comprises a hydraulic brake unit (11) provided with a coupling (12) for a screwdriver to be tested and angle and torque measurement transducers (15). The brake unit (11) is supplied by a proportional electrovalve (16) under the control of a PID controller (19) which receives an electrovalve control signal (22) from a control unit (26) so as to follow braking curves depending on the angle of rotation and/or torque measured. The bench comprises a memory (21) for storing different sets of parameters for the PID controller (19), which can be selected by the control unit (26) so as to have different control characteristics. A method for controlling the bench is also described.

11 Claims, 3 Drawing Sheets

(51) Int. Cl.
*G01L 3/20* (2006.01)
*B25H 1/00* (2006.01)
*B25B 21/00* (2006.01)

(56) References Cited

U.S. PATENT DOCUMENTS

| | | | | |
|---|---|---|---|---|
| 4,782,726 A * | 11/1988 | Ryder | ................ | B23P 19/06 |
| | | | | 81/57.24 |
| 5,886,246 A * | 3/1999 | Bareggi | ............... | G01L 25/003 |
| | | | | 73/1.09 |
| 6,202,028 B1 * | 3/2001 | Crane | ................ | G01L 25/003 |
| | | | | 702/41 |
| 6,715,361 B2 * | 4/2004 | Chiapuzzi | ............ | G01L 5/0042 |
| | | | | 73/760 |
| 6,718,831 B2 | 4/2004 | Chiapuzzi et al. | | |
| 7,958,611 B2 | 6/2011 | Friberg et al. | | |
| 8,040,130 B2 * | 10/2011 | Chiapuzzi | ............ | G01L 25/003 |
| | | | | 324/207.2 |
| 8,453,519 B2 * | 6/2013 | Zhang | ................ | G01L 5/0042 |
| | | | | 73/862.08 |
| 9,702,797 B2 * | 7/2017 | Yang | ................. | G01N 3/22 |
| 2003/0056605 A1 | 3/2003 | Chiapuzzi et al. | | |
| 2003/0057034 A1 | 3/2003 | Chiapuzzi et al. | | |
| 2004/0162658 A1 * | 8/2004 | Newman | ............... | B66C 13/50 |
| | | | | 701/50 |
| 2005/0114001 A1 * | 5/2005 | Newman | ............... | B66C 13/50 |
| | | | | 701/50 |
| 2009/0138130 A1 * | 5/2009 | Aigner | ................ | B60R 16/03 |
| | | | | 700/282 |
| 2009/0265135 A1 | 10/2009 | Hetzel | | |
| 2010/0039053 A1 * | 2/2010 | Matsutani | ............ | B23P 19/066 |
| | | | | 318/68 |
| 2010/0116067 A1 | 5/2010 | Chiapuzzi | | |
| 2010/0204871 A1 * | 8/2010 | Bange | ................ | H02M 3/156 |
| | | | | 701/31.4 |
| 2011/0247434 A1 * | 10/2011 | Carlin | ................ | G01L 5/24 |
| | | | | 73/862.21 |
| 2015/0174750 A1 * | 6/2015 | Hosking | ................ | B25F 5/00 |
| | | | | 173/170 |
| 2016/0001411 A1 * | 1/2016 | Alberti | ................ | B25B 23/14 |
| | | | | 700/188 |
| 2016/0138987 A1 * | 5/2016 | Traballoni | ............ | G01L 25/003 |
| | | | | 73/121 |
| 2017/0363500 A1 | 12/2017 | Boccellato | | |

OTHER PUBLICATIONS

Machine translation of CN 103713519 A.*
International Search Report in International Application No. PCT/IB2015/059825, dated Apr. 11, 2016.
Non-Final Office Action dated Mar. 12, 2018 for U.S. Appl. No. 15/539,428.
International Search Report in International Application No. PCT/IB2015/059828, dated Apr. 11, 2016.

* cited by examiner

SCREWDRIVER TEST BENCH

This application is a National Stage of International Application PCT/IB2015/059828, filed Dec. 21, 2015, published Jun. 30, 2016, under PCT Article 21(2) in English; which claims the priority of Italian Application No. MI2014A002239, filed Dec. 23, 2014. The contents of the above-identified applications are incorporated herein by reference in their entireties.

The present invention relates to an innovative test bench for screwdrivers.

In the prior art it is well-known that there exists the need to check periodically power screwdrivers in order to ensure that they have the necessary operational uniformity and precision.

It is customary to use, for the checking procedure, test benches provided with a coupling which is braked in a controlled manner in order to simulate a screw being tightened while the screwdriver acts on it.

Essentially, the screwdriver is operated on the bench coupling. The coupling is connected to a brake which is usually hydraulically controlled and, via a proportional servo-valve, is suitably driven by the electronic system with which the bench is equipped so as to comply with the predefined parameters for simulation of a type of screw joint, allowing the system to detect the behaviour of the screwdriver by measuring the torque and angle values during the test cycle.

The servo-valve modulates the braking action by regulating the hydraulic pressure which acts on the brake pistons such that it is operated in the manner required and which is supplied to it in the form of an electric signal.

By simulating the tightening of a mechanical joint, the brake offers a resistance to the rotation which is proportional to the tightening angle. The greater the angle, the greater will be the torque which the screwdriver must apply to the brake in order to cause it to rotate until the set tightening torque is reached.

In order to achieve this behaviour, the control system supplies the proportional valve with a signal which is increasingly greater depending on the angle moved through, in accordance with a suitable braking curve.

However the parameters which the braked coupling of a test bench must satisfy in order to obtain a correct simulation of the different possible behaviour of the various types of screw connections to which the screwdriver must be applied are many and of a varying nature.

For example, the control system must be able to simulate the behaviour of mechanical joints of different types: these ranging from "rigid" joints where the tightening torque is reached with small angles of rotation (for example of the order of 30 degrees) to "soft" joints where the torque is reached after large angles of rotation (for example of the order of 720 degrees or more). In addition to this "variability" of the simulation conditions, it is also necessary to take into account the behavioural "variability" of the screwing servo means to be controlled which depends both on the speed of rotation and on the tightening parameters set on the screwdriver.

In order to obtain a good control over the tightening action, adjustment of the pressure in the brakes is generally performed by the analog proportional valve via a PID type control system. However, in practice it can be noted how there is not any one particular combination of the parameters P, I and D (defined via a dedicated analog electronic circuit) which is optimum for each type of simulation. It is thus necessary to have several braked couplings, each with a given PID control circuit in order to simulate a particular tightening behaviour. This results in the need to have several different test benches, or else test benches with several different braked couplings and each with its own different control system, along with the associated purchase and management costs and not insignificant volume-related problems, in particular in the case of large-scale users of screwdrivers, such as companies with assembly lines in the automobile sector.

The general object of the present invention is to provide a test bench which allows a greater degree of flexibility in the simulation parameters so as to allow, for example, the simulation of a wider range of tightening behaviours.

In view of this object the idea which has occurred is to provide, according to the invention, a test bench for screwdrivers comprising a hydraulic brake unit provided with a coupling for a screwdriver to be tested and angle and torque measurement transducers, the brake unit being supplied by a proportional electrovalve under the control of a PID controller which receives an electrovalve control signal from a control unit so as to follow braking curves depending on the angle of rotation and/or the torque measured, characterized in that it comprises a memory for storing different sets of parameters for the PID controller which can be selected by the control unit.

Still according to the invention, the idea which has occurred is to provide a method for controlling a test bench for screwdrivers comprising a hydraulic brake provided with a coupling for a screwdriver to be tested and angle and torque measurement transducers, the brake being supplied by a proportional electrovalve under the control of a PID controller which receives an electrovalve control signal from a control unit so as to follow braking curves depending on the angle of rotation and/or the torque measured, characterized in that it comprises the steps of storing in an electronic memory of the bench a plurality of different sets of parameters for the PID controller and selecting and entering in the PID controller the parameters of a set of the plurality depending on the test to be performed and/or the screwdriver to be tested.

In order to illustrate more clearly the innovative principles of the present invention and its advantages compared to the prior art, an example of embodiment applying these principles will be described below with the aid of the accompanying drawings. In the drawings.

Figure 1:
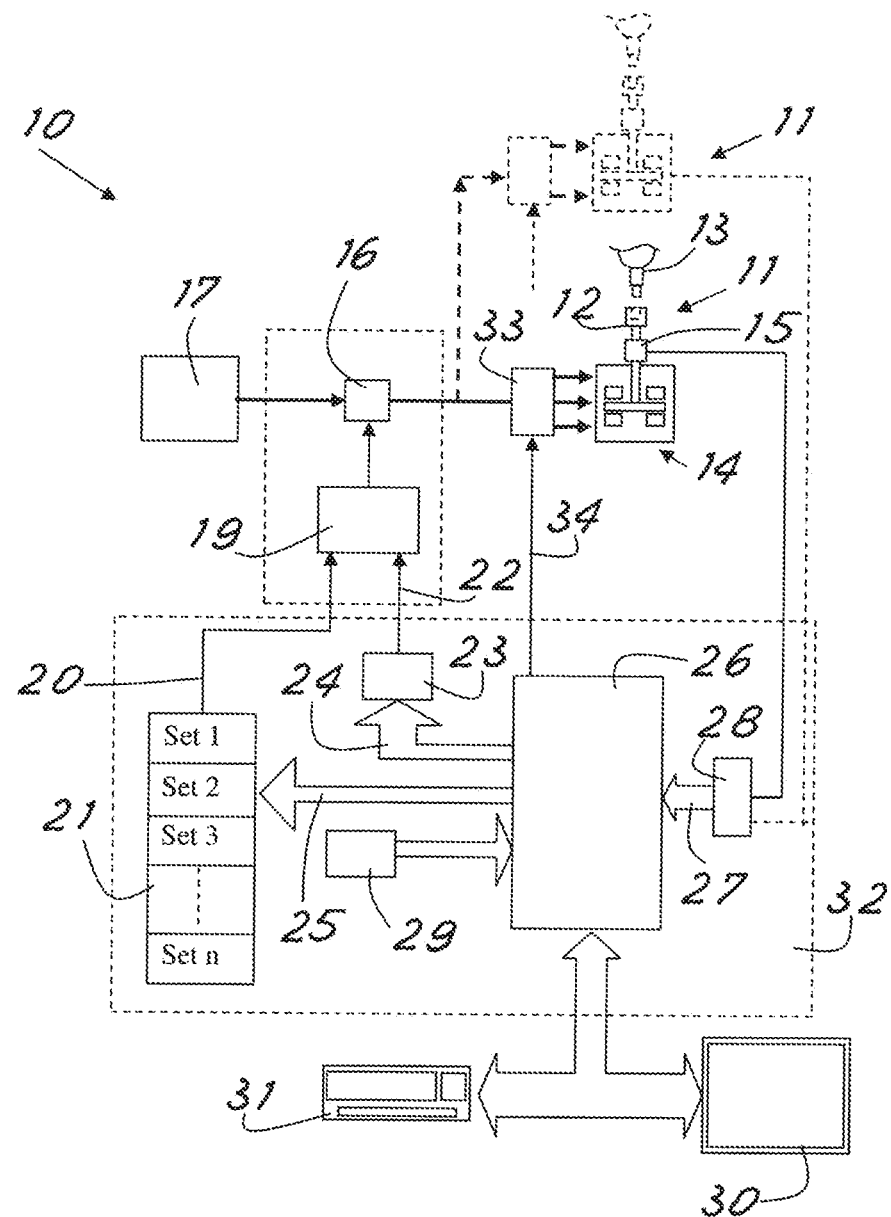
FIG. 1 shows a schematic view of a test bench according to the invention.

With reference to the figures, FIG. 1 shows schematically a test bench—denoted overall by 10—provided in accordance with the invention.

The bench 10 comprises a braking unit 11 provided with a coupling 12 (where necessary of the replaceable type) for engagement with the corresponding end of a screwdriver 13 to be tested. The braking unit comprises a hydraulic brake 14 and a known transducer unit or torque and angle sensor 15 connected to the brake (advantageously arranged between the coupling 12 and the brake 14).

The brake receives the actuating fluid via an electrovalve 16 which receives in turn the fluid from a suitable source 17 supplying pressurized fluid, for example a suitable hydraulic pump.

The electrovalve 16, which is advantageously of the proportional type, is electrically controlled by a control unit or PID (proportional, integral, derivative) controller of the digital type which receives digital information 20 regarding the characteristic parameters of the PID control (for example, as may be imagined by the person skilled in the art, the derivation time constant Td, the integration time constant Ti and the proportionality constant Kp) from a parameter memory 21. The memory for storing the parameters may contain sets of PID parameters already predefined for various types of screwdriver and/or tests to be carried out. In some cases, some of the PID control parameters may also be set to zero, namely one of the three components P, I or D may be zeroed. For example the derivative action may be eliminated. As will become clear below, the parameters of each set may be stored beforehand, for example at the factory, within the memory, and a particular size or type of screwdriver associated with each set, so that the desired set may be recovered from the memory, for example depending on the measurement requirements entered by the user.

The PID controller 19 also receives the control signal 22 for the desired opening of the electrovalve 16. This signal will follow a curve which is a function of the desired opening progression, as will become clear below. Preferably, the signal 22 is a voltage signal which depends on the desired opening and which will be processed by the unit 19 according to the PID logic entered so as to supply a final control signal to the electrovalve with the appropriate corrections of the retraction errors, as known for PID control systems.

In the case where an analog voltage is used as signal 22, a digital/analog conversion unit 23 may be present and emits the analog signal 22 depending on digital data or signals 24.

The signals 24 and digital control signals 25 of the memory 21 for selection of the PID parameters are provided by a command unit or processing and control unit 26 which also receives signals 27 from the torque and angle sensors 15, optionally via a suitable conversion unit 28 so as to be able to perform the measurements and follow the curves for the torque/angle/velocity, as known for screwdriver test benches.

A further memory 29 contains advantageously the braking curve or curves which are desired for the test or the tests which may be carried out by the bench depending on the PID parameters entered.

The processing and control unit 26 is advantageously connected to known user interface peripheral units, such as a screen 30 (optionally touch-screen) and a keyboard 31, for entering the commands and for displaying the results.

The user may thus select, via the user interface 29, 30 and the unit 26, the desired set of parameters in the memory 21, which is loaded into the PID controller 19. The unit 26 also loads from the memory 29 the appropriate control curve, for example depending on the angle and/or torque, detected by the suitable sensors 15, and, if necessary, the time.

Obviously, in addition to being separate hardware units, the memories 21 and 29, the digital/analog and analog/digital conversion units 24 and 28 and the processing unit 26 may also form part of a suitably programmed digital microprocessor system, for example realized with a programmable industrial control board, known per se.

The PID controller 19 may also form part of the system 32 or may be an external component, advantageously incorporated in the electrovalve 16, such that the electrovalve 16 becomes a digital PID controlled electrovalve unit. The interface for communication of the parameters with the digital information 20 may be a standard digital interface of the known type (preferably of the industrial type) such as an EtherCAT, CAN bus, serial or other type of communication interface. In the case of a PID controller outside the system 32, this controller may be realized by means of a suitable digital microcontroller system programmed to perform the PID control using the parameters transmitted to it via the digital signals 20 and the control signal 22, as may be easily imagined by the person skilled in the art of PID control procedures.

The same memory 21 for the parameter sets may be a memory inside the PID controller 19 of the valve rather than the board 32, and the selection signals 25 may directly reach the digital system which forms the controller 19.

As well as a separate system, the PID controller may also be realized via software in the same processing unit 26, as may now be easily imagined by the person skilled in the art. The processing unit 26 may also be realized in the form of a personal computer, provided with suitable input and output interfaces and suitably programmed, as may be now easily imagined by the person skilled in the art.

With the innovative bench described it is for example advantageously possible to store different sets of PID parameters and suitably select them depending on the activity to be performed. The sets may be stored directly in a memory in the servo-valve, if provided with an integrated control system, or in a memory in the bench control system.

It is therefore clear how the bench may set the PID control of the brake within a wide range of values depending on needs, so that the braking system may be adapted to the various types of screwing operation to be simulated.

Moreover, with a system according to the invention, the PID parameters may also be varied dynamically during the measurement or measurements rapidly and in sequence.

Advantageously, as will be further clarified below, the brake 14 may be provided with a plurality of hydraulic actuators supplied by the electrovalve 16 via a controlled distributor 33 which receives from the unit 26 suitable signals 34 for selecting the brake actuators to which the operating fluid is to be supplied.

This allows, for example, progressive adjustment of the brake action so as to manage a wider range of screwdrivers, in particular by combining this progressive adjustment of the action of the hydraulic part of the brake with the possibility of varying the behaviour of the system by means of different preset values of the PID controller and the operating curves of the electrovalve.

Figure 2:
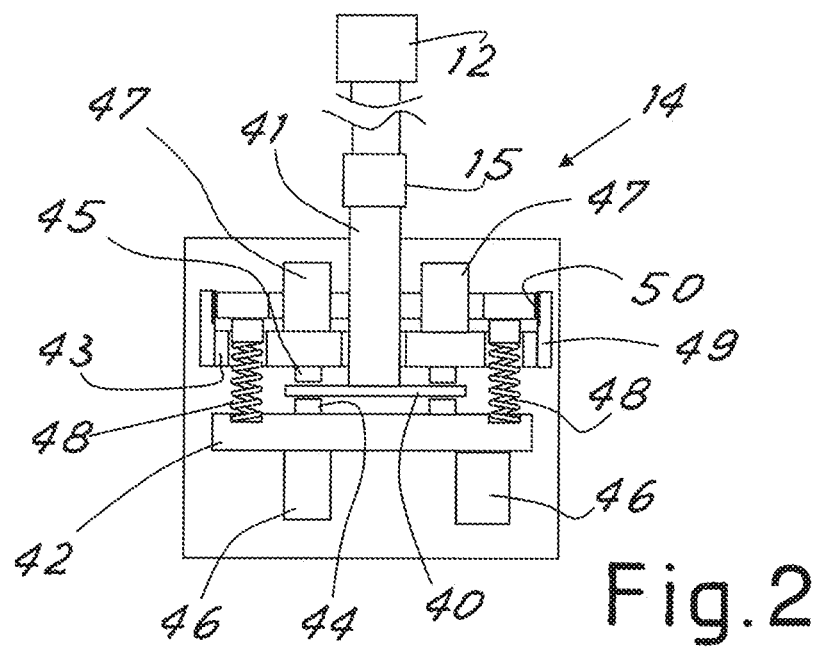
FIG. 2 shows a schematic longitudinally sectioned view of a braking unit of the test bench according to FIG. 1.

FIG. 2 shows an advantageous embodiment of the brake 14. In this embodiment, the brake comprises a disk 40 axially connected to the coupling 12 via a shaft 41 on which the sensor unit 15 (known per se) is provided for measuring the torque transmitted between brake and coupling and for measuring the angle of rotation of the shaft. The disk 40 therefore rotates axially, being moved by the screwdriver which is connected to the coupling 12 for the test.

On the opposite sides of the disk 40 the brake comprises a pair of braking plates 42, 43 which are mounted so as to be slidable towards each other along the axis of rotation of the disk. The sides of the plate directed towards the disk are provided (advantageously distributed circumferentially around the axis of rotation of the disk) with braking surfaces 44 which are made of suitable friction material and are pressed in a controllable manner against the opposite sides of the disk so as to brake it.

The friction material may consist of different known types. It has, however, been found to be particularly advantageous to use carbon surfaces, which in particular are dry. Alternatively, however, oil-wetted carbon surfaces may also be used.

The braking movement of the plates towards the disk is controlled by respective groups of actuating pistons 46, 47 against the action of a plurality of reaction springs 48 which are circumferentially distributed around the axis of the disk and which, with the pistons at rest, keep the plates 42, 43 separated from the disk. Preferably, the compression of the springs 48 between the plates is adjustable so as to provide a predefined pre-compression value at rest.

For adjustment of the pre-compression of the springs, as schematically shown in FIG. 2, advantageously one end of the springs 48 acts directly against one of the plates, while the opposite end acts on the other plate via an adjusting ring 49 connected by means of a peripheral thread 50 to the plate so that, when the ring is axially rotated around the shaft 41, the ring moves axially with respect to the plate and compresses simultaneously all the springs 48 to a greater or lesser degree. Sliding elements are advantageously provided between ends of the spring and the adjusting ring so as to allow rotation of the ring without laterally distorting the springs.

Figure 3:
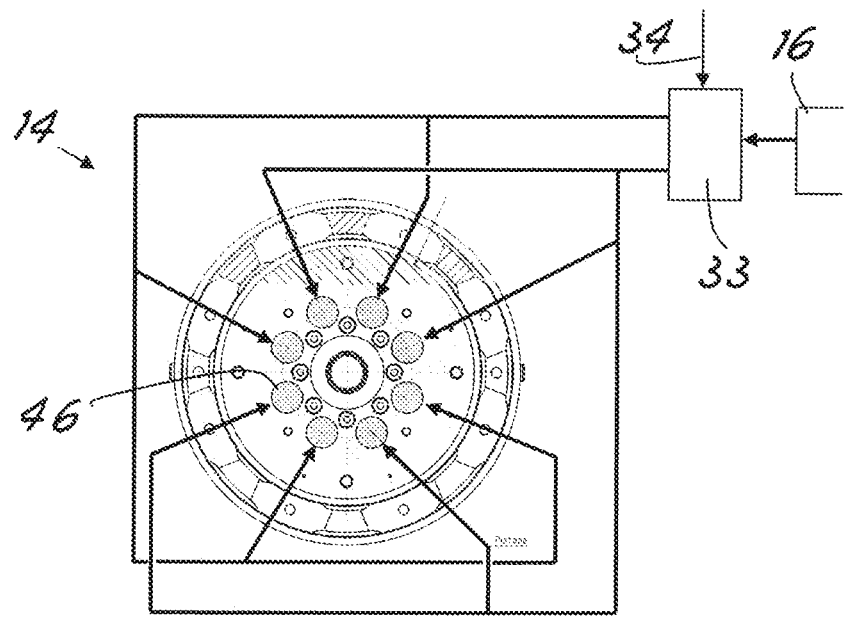
FIG. 3 shows a schematic cross-sectional view of the unit according to FIG. 2.

Advantageously, the pistons for performing the movement of the plates towards each other and against the disk 40 consist of a plurality and are distributed circumferentially around the axis of rotation of the disk, as can be clearly seen in FIG. 3.

Moreover, advantageously, the pistons can be selectively activated in groups so as to have different braking torques. In particular, the pistons may be connected in groups to the valve 16 by means of the distributor 33 which is operationally controlled by the signal 34 of the control unit 26. For example, it has been found to be advantageous to divide the pistons of each plate into two alternate groups, as schematically shown in FIG. 3.

In this way it is possible to reduce in a controllable manner the number of pistons acting on each plate.

FIG. 3 shows an example of connection of the pistons in two identical groups, although it is possible to form two groups with a different number of pistons and also more than two groups of pistons, as required. The total number of pistons may also be different from that schematically shown in the figures.

Owing to the possibility of excluding in a controllable manner some pistons of the brake it is thus possible to optimize the use of the pressure of the electrovalve when tests with braking torques lower than the maximum torque which can be generated by the brake are required. As a result it is possible to have always a high resolution during control of the braking torque.

In fact, by excluding some of the pistons of the plurality a smaller braking capacity is obtained, but in any case the entire resolution range of electrovalve operation is made use of so that the system is more precise for example when used in the lower torque range.

The braking system is thus supplied by the proportional electrovalve which receives the command from the PID controller and this command is always equal to 0-100% of the maximum braking capacity of the brake unit. This maximum braking capacity depends however on the number of pistons used.

For example, it may be decided to exclude some of the pistons and obtain the result where 0-100% control (for example 0 to 10V) corresponds to 0-30% of the maximum capacity of the brake, which is thus progressively adjusted. In this way it is possible to modulate the maximum torque of the braking system depending on the type of simulation which is to be performed and/or the dimensions of the screwdriver being tested, optimizing the reaction times and the inertia of the system.

For example, with a system having a maximum pressure output by the electrovalve equal to 100 bar and with the braking system having two groups of pistons respectively formed by three and six pistons for each plate, the brake may be designed for example with dimensions such as to provide a maximum braking torque of 60 Nm when both groups of pistons are supplied by the valve.

By operating this brake so as to function for example with the groups of three pistons, with the same maximum pressure of the electrovalve equal to 100 bar, the brake will provide instead a maximum braking torque of 20 Nm.

In this way, using the same control for the electrovalve and the same braking system dimensionally designed for 60 Nm, it is possible to reduce the power and make simulation more manageable by making full use of the capacity of the electrovalve. As a result, it is possible to increase the range of screwdrivers which may be tested using the same bench and the same brake.

Figure 4:
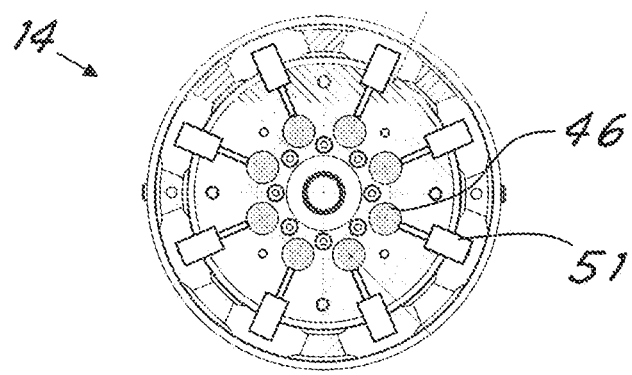
FIGS. 4, 5 and 6 show schematic cross-sectional views of variations of embodiment of the unit according to FIG. 2.

FIG. 4 shows in schematic form a variation of embodiment where the groups of pistons are mechanically, rather than hydraulically, selected. In this variant, each piston comprises a locking actuator 51 which is engaged in a controllable manner, transversely with respect to the thrusting stroke of the respective piston, so as to lock it in the rest condition. The actuators 51 are operationally controlled by the selection signal 34 instead of the hydraulic distributor 33, so as to have the same function of regulation of the brake action described above. The actuators may be electrical (for example solenoids) or hydraulic (for example pistons). In the first case, the electrical selection signals 34 may control the actuators either directly or via a suitable power unit (not shown), while in the second case a known electrically controlled hydraulic distributor may be used, in a similar manner to the distributor 33, said unit advantageously receiving the pressurized fluid from the source 17.

Figure 5:
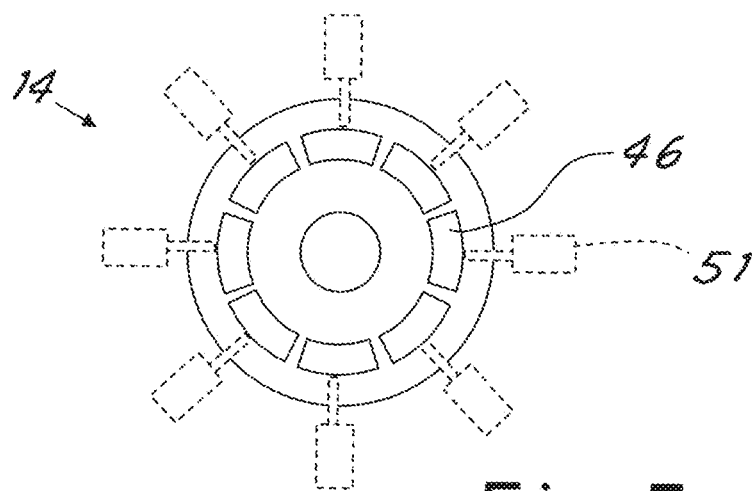

As schematically shown in FIG. 5, the pistons may also have a form other than the conventional cylindrical form and, for example, may be realized as segments of a circular rim. In any case, the regulated operation may be achieved as described above, with regulation of the piston operating fluid or via electrical or hydraulic locking actuators for stopping the pistons.

Figure 6:
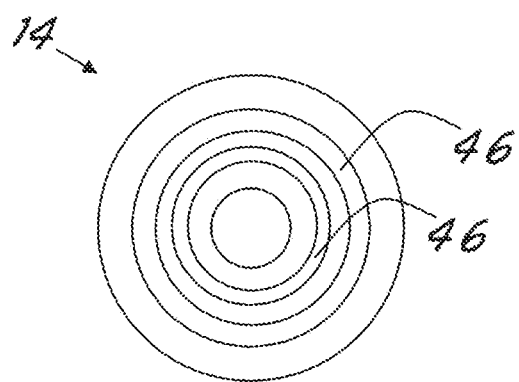

As schematically shown in FIG. 6, the pistons may also be realized in the form of concentric circular rims, such that there are several pistons 46 arranged one inside the other.

Obviously, the bench may also comprise a plurality of brakes with various dimensions for testing an even wider range of screwdrivers, as schematically shown in broken lines in FIG. 1. The control system will act on the prechosen brake as already described above and the control parameters may be chosen, as required, depending on the type of brake used.

At this point it is clear how the predefined objects have been achieved.

After storing in the bench memory (for example at the factory) the various sets of PID parameters and the performance curves for the different tests which are to be carried out using the bench, optionally according to the type of screwdrivers, the brakes and the number of pistons which may be selected, it is possible to use the bench by selecting the desired test via the user interface 30, 31.

The control unit will select the sets of parameters and the angle and/or torque characteristics or curves suitable for the test and the user may apply the screwdriver to the coupling 12 and carry out the test, the result of which will be shown in a manner known per se on the screen 30.

In the case of a brake with selectable pistons, depending on the test to be performed and/or the characteristics of the screwdriver, the control unit 26 may also select the maximum braking capacity of the brake by operationally controlling the various groups of pistons, for example so as to keep the operating resolution of the electrovalve always high even in the case of small maximum braking torque values.

As a result of the above, the bench may perform measurements of a wide range of screwdrivers in a precise and reliable manner and with minimum manual settings on the part of the user.

Obviously the description above of an embodiment applying the innovative principles of the present invention is provided by way of example of these innovative principles and must therefore not be regarded as limiting the scope of the rights claimed herein. For example, the brake structure may be different from that shown.

The invention claimed is:

1. Test bench for screwdrivers comprising a hydraulic brake unit (1) provided with a coupling (12) for a screwdriver to be tested and angle and torque measurement transducers (15), the brake unit (1) being supplied by a proportional electrovalve (16) under the control of a PID controller (19) which receives an electrovalve control signal (22) from a control unit (26) so as to follow braking curves depending on the angle of rotation and/or torque measured, characterized in that it comprises a memory (21) for storing different sets of parameters for the PID controller (19), which can be selected by the control unit (26).

2. The test bench according to claim 1, characterized in that the PID controller is a digital PID controller which receives the sets of parameters via a digital communication interface.

3. The test bench according to claim 2, characterized in that the PID controller receives the control signal (22) for the electrovalve (16) in the form of an analog signal.

4. The test bench according to claim 1, characterized in that the brake unit comprises a disk (40) axially connected to the coupling (12) so as to be rotated by a screwdriver to be tested, and braking plates (42, 43) situated on the opposite sides of the disk (40) so as to be pushed operationally with their braking surfaces (44, 45) against the opposite sides of the disk (40) by means of a plurality of pistons (46, 47) supplied with fluid by the proportional electrovalve (16).

5. The test bench according to claim 4, characterized in that the pistons (46, 47) of the plurality can be selectively activated under the control of the control unit (26) so as to select the maximum braking torque of the brake.

6. The test bench according to claim 5, characterized in that the pistons (46, 47) of the plurality can be selectively activated under the control of the control unit (26) by means of a hydraulic distributor connected between the electrovalve (16) and groups of pistons (46, 47).

7. The test bench according to claim 5, characterized in that the pistons (46, 47) of the plurality can be selectively activated under the control of the control unit (26) by means of controllable actuators (51) for locking the pistons in a rest position.

8. The test bench according to claim 4, characterized in that the plates are pushed by the pistons against the sides of the disk against the action of adjustable springs (48).

9. The test bench according to claim 8, characterized in that the springs (48) are adjustable by means of an adjusting ring (49) mounted on one of the two plates and rotatable axially relative to the disk (40) by means of a thread (50) so as to move correspondingly in an axial direction with respect to the plate on which it is mounted and push against one end of the springs so as to pre-compress more or less all the springs.

10. Method for controlling a test bench for screwdrivers comprising a hydraulic brake provided with a coupling for a screwdriver to be tested and angle and torque measurement transducers, the brake being supplied by a proportional electrovalve under the control of a PID controller, which receives an electrovalve control signal from a control unit so as to follow braking curves depending on the angle of rotation and/or the torque measured, characterized in that it comprises the steps of storing in an electronic memory of the bench a plurality of different sets of parameters for the PID controller and selecting and entering in the PID controller the parameters of a set of the plurality depending on the test to be performed and/or the screwdriver to be tested.

11. The method according to claim 10, comprising the further step of providing the brake with a plurality of pistons (46, 47) for performing braking, supplied by the electrovalve (16), and selecting in a controllable manner the number of pistons of the plurality to be operated with the electrovalve (16) so as to vary the maximum braking torque of the brake.

\* \* \* \* \*